(12) United States Patent
Eden

(10) Patent No.: US 7,071,005 B1
(45) Date of Patent: Jul. 4, 2006

(54) METHOD AND DEVICE FOR CONCENTRATING SELECTED GROUPS OF MICROORGANISMS

(75) Inventor: Ruth F. Eden, Ann Arbor, MI (US)

(73) Assignee: Centrus International, Inc., Ann Arbor, MI (US)

( * ) Notice: Subject to any disclaimer, the term of this patent is extended or adjusted under 35 U.S.C. 154(b) by 0 days.

(21) Appl. No.: 09/763,578

(22) PCT Filed: Aug. 23, 1999

(86) PCT No.: PCT/US99/18618

§ 371 (c)(1),
(2), (4) Date: Jul. 28, 2001

(87) PCT Pub. No.: WO00/10702

PCT Pub. Date: Mar. 2, 2000

Related U.S. Application Data

(60) Provisional application No. 60/097,627, filed on Aug. 24, 1998.

(51) Int. Cl.
*G01N 33/53* (2006.01)

(52) U.S. Cl. .................... 436/518; 436/541; 435/7.1; 435/4; 435/7.2; 435/34; 435/40.51; 435/383; 435/394; 435/395; 435/403; 435/287.1; 435/289.1; 422/56; 422/58; 422/68.1; 422/99; 422/101; 422/103; 422/104

(58) Field of Classification Search ............. 422/58, 422/68.1, 99, 101, 103, 104, 56; 435/7.1, 435/4, 7.2, 34, 40.51, 383, 394, 395, 403, 435/287.1, 289.1; 436/518, 541
See application file for complete search history.

(56) References Cited

U.S. PATENT DOCUMENTS

| 3,840,345 | A | | 10/1974 | Andre' |
|---|---|---|---|---|
| 4,230,685 | A | * | 10/1980 | Senyei et al. |
| 4,677,055 | A | * | 6/1987 | Dodin et al. |
| 4,695,393 | A | * | 9/1987 | Whitehead et al. |
| 4,818,687 | A | | 4/1989 | Groopman et al. |
| 4,859,611 | A | | 8/1989 | Groopman et al. |

(Continued)

FOREIGN PATENT DOCUMENTS

WO 95/21241 * 8/1995

OTHER PUBLICATIONS

Yang et al., "Kinetics and Stability of GM-CSF Production by Recombinant Yeast Cells Immobilized in a Fibrous-Bed Bioreactor," Biotechnol Prog. vol. 12, pp. 449-456 (1996).

(Continued)

*Primary Examiner*—Bao-Thuy L. Nguyen
(74) *Attorney, Agent, or Firm*—Ian C. McLeod

(57) ABSTRACT

A method and device are described to concentrate target organisms from a mixture of organisms. Beads (1) made of material such as nylon, polystyrene or glass are coated with antibodies of specific microorganisms. The beads (1) are contained in an enclosure (2) surrounded by grid material (4). The pore size of the grid is smaller than the size of the beads, to assure that the beads stay within the grid material and larger than the size of the microorganisms to allow the interaction of the microorganisms with the beads. A rod (5) is attached to the upper part of the enclosure (2) allowing the agitation of the device inside he growth medium containing the target organisms.

15 Claims, 1 Drawing Sheet

U.S. PATENT DOCUMENTS

| | | |
|---|---|---|
| 4,931,401 A | 6/1990 | Safi |
| 4,959,307 A | 9/1990 | Olson |
| 4,963,468 A | 10/1990 | Olson |
| 4,983,517 A * | 1/1991 | Kim et al. .................... 435/41 |
| 5,009,852 A | 4/1991 | Kita et al. |
| 5,081,035 A * | 1/1992 | Halberstadt et al. |
| 5,085,987 A | 2/1992 | Olson |
| 5,085,988 A | 2/1992 | Olson |
| 5,139,933 A | 8/1992 | Green et al. |
| 5,186,824 A | 2/1993 | Anderson et al. |
| 5,260,193 A | 11/1993 | Olson |
| 5,260,194 A | 11/1993 | Olson |
| 5,409,822 A * | 4/1995 | Scott et al. |
| 5,491,068 A * | 2/1996 | Benjamin et al. |
| 5,556,756 A | 9/1996 | Olsen et al. |
| 5,567,615 A * | 10/1996 | Degen et al. |
| 5,616,467 A | 4/1997 | Olsen et al. |
| 5,695,946 A * | 12/1997 | Benjamin et al. |
| 5,705,390 A * | 1/1998 | Kadouri et al. ............. 435/395 |
| 5,776,710 A | 7/1998 | Levine et al. |
| 5,866,006 A * | 2/1999 | Lihme et al. |
| 5,998,184 A * | 12/1999 | Shi ........................... 435/176 |
| 6,153,373 A | 11/2000 | Benjamin et al. |
| 6,395,537 B1 * | 5/2002 | Eden et al. |
| 6,489,092 B1 | 12/2002 | Benjamin et al. |
| 2004/0043116 A1 | 3/2004 | Cohen |

OTHER PUBLICATIONS

Yang et al., "Xanthan Gum Fermentation by *Xanthomonas campestris* Immobilized in a Novel Centrifugal Fibrous-Bed Bioreactor," Biotechnol Prog. vol. 12, pp. 630-637 (1996).

Lewis et al., "Continuous propionic acid fermentation by immobilized *Propionibacterium acidipropionici* in a novel packed-bed bioreactor," Biotechnology and Bioengineering, vol. 40, pp. 465-474 (1992).

Search Report for International Application PCT/US99/18618.

Preliminary Examination Report for International Application PCT/US99/18618.

* cited by examiner

METHOD AND DEVICE FOR CONCENTRATING SELECTED GROUPS OF MICROORGANISMS

This application is a 371 of PCT/US99/18618 filed Aug. 23, 1999 which claims benefit of Provisional application Ser. No. 60/097,627 filed Aug. 24, 1998.

BACKGROUND

1. Field of Invention

This application is based on provisional patent application Ser. No. 60/097,627, filed Aug. 24, 1998.

The present invention relates to products and processes used for the detection of microbes in a sample. More specifically, the present invention provides a method and device for aiding in the detection of the presence of specific microbial contamination in food samples, clinical specimens and other products.

2. Prior Art

It is necessary to test various substances, such as foods, beverages, pharmaceuticals, cosmetics, water, and body fluids for microbial contamination, especially with certain pathogenic bacteria. Recent outbreaks of foodborne illness, implicating a variety of foods contaminated with pathogenic bacteria, such as *E. coli* 0157:H7, *Salmonella, Listeria, Campylobacter jejuni*, and *Cyclospora*, have underscored the need for rapid methods for microbiological analysis. Microbiological analysis is critical for assessment of safety and quality, to determine efficiency of manufacturing, and conformance with regulations.

The increased scope, significance, and need for microbiological testing served to reveal the limitations and drawbacks of conventional methods. Classical methods for determining the presence of pathogenic bacteria in samples are taking typically several days to perform. It is desired to provide rapid detection of especially pathogenic bacteria causing illnesses.

Since the desired sensitivity for most assays for pathogenic bacteria is less than one such organism in 25 grams of product, most testing methods rely on an initial enrichment step. The indigenous microflora that is usually present in many foods at high levels often interferes with the selective isolation and identification of pathogenic bacteria. Food processing such as heating, cooling, drying, freezing, addition of preservatives and other causes can sub-lethally injure bacterial cells. These injured cells are extremely sensitive to the ingredients used in selective microbiological media. Therefore, in many assays the process starts with pre-enrichment, in which the sample is incubated in a nutritious, non-selective medium to allow the resuscitation of injured or stressed bacteria. This step is followed by a selective enrichment step where the bacteria of interest are allowed to grow while the indigenous microflora is suppressed. The enrichment procedure is followed either by conventional plating methodology or a variety of more modern and rapid methods such as DNA amplification or immunoassay.

It is therefore desired to separate at an early stage the target organisms from the other flora present in the product. One such approach is the utilization of the immuno-magnetic separation technique, involving the utilization of immuno-magnetic particles specific for the target organisms. Magnetic beads with antibodies affixed to their surfaces are mixed with the sample containing the target organism. This organism will bind to the bead surfaces via the antibodies. The organism-bead complex is pulled out of the solution by a magnet, to concentrate the microorganisms.

U.S. Pat. No. 4,230,685 describes magnetically responsive microspheres having protein A associated with the outer surface. The microspheres are reacted with antibodies selective to cells, bacteria or viruses to be separated from a mixed population. The microorganism will attach to the antibody and thereby to the microspheres, and the microspheres are then used in a magnetic separation procedure. The preferred microspheres are prepared from a mixture of albumin, Protein A, and magnetic particles. The microspheres are prepared so that the Protein A is present in the exterior surface of the antibody binding. U.S. Pat. No. 4,695,393 describes a process for the preparation of such magnetic beads, which can be used in separation of microorganisms.

U.S. Pat. Nos. 5,491,068 and 5,695,946 describe a method characterized by antibody capture of the organism of interest by the application of specialized magnetic beads. It entails the incubation of the capture cells to form colonies; removal of material from the colonies with colony lift membrane; and detection of the colony material on the membrane sheet by the use of labeled antibodies, PCR or nucleic acid probes. The main problem with this method is the low sensitivity of one organism per gram. This low sensitivity is inherent in the methodology and is 50–100 fold lower than the desired sensitivity for most food pathogens.

U.S. Pat. No. 4,677,055 describes a process for concentrating bacteria utilizing magnetic gel to which anti-specific antigenic determinant antibodies are coupled. It involves the steps of obtaining medium containing the organisms possessing specific antigenic determinants and bringing them in contact with particles of the magnetic gel. This step is followed by the separation of the gel from the medium by magnetic means and inoculation into new medium.

In general there are a number of problems associated with magnetic beads. One such problem results from the small size of such beads (3–10 μm) and the large volume of the medium (250–3,000 ml). As a result it is impossible to remove the magnetic beads from such a large volume. Therefore, many procedures either use a lower sample volume (thereby reducing the sensitivity of the assay) or allow some time (8–18 hours) of pre-enrichment followed by the removal of 1–5 ml of solution for concentration of the target organisms. Another problem associated with the magnetic beads is the fact that they get coated with fat and proteins making it difficult to be collected with a magnet. The process of separating the beads from the medium and washing the unattached bacteria is labor intensive, and creates a contamination hazard of both laboratory surfaces and the beads.

OBJECTS AND ADVANTAGES

It is, therefore, an object of the invention to provide a method and device that can be utilized with a large volume of media, to concentrate a target organism. It is another object of the invention to provide a method that is less labor intensive, more rapid and will lend itself to automation.

Still further objects and advantages will become apparent from a consideration of the ensuing description and accompanying drawings.

DESCRIPTION

Figure 1:
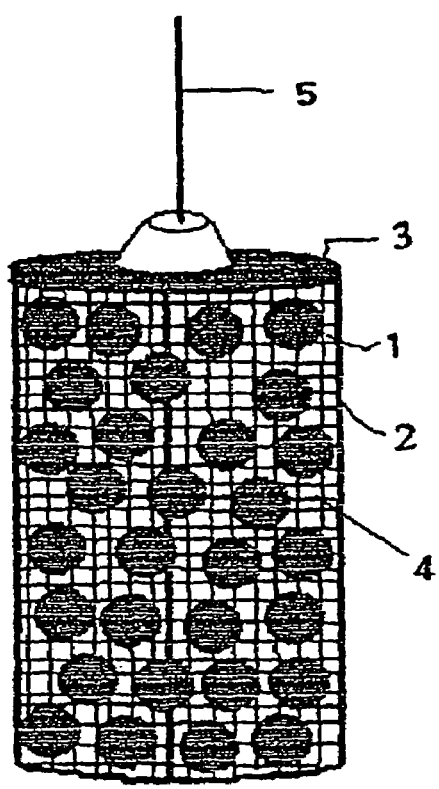
FIG. 1 shows a side view of the preferred device utilized to concentrate target organisms.

FIG. 1 shows the preferred embodiment of a device for the separation of the target organisms from a suspension containing a mixture of organisms. Beads 1 are made of materials such as nylon, polystyrene or glass. The beads are coated with antibodies to specific microorganisms such as *Salmonella, E. coli* 0157:H7 and *Listeria*. A cylindrical enclosure 2 is designed to contain the beads. The enclosure is constructed from a frame 3 supporting a grid 4 covering the frame. The grid's pore size is smaller than the size of the beads to assure that the beads stay within the enclosure 2. However, the pore size is large enough to allow bacteria to freely pass into the enclosure. A rod 5 is attached to the upper part of the enclosure. The rod 5 allows the enclosure 2 to move in the solution and for subsequent removal of the device from the solution.

Figure 2:
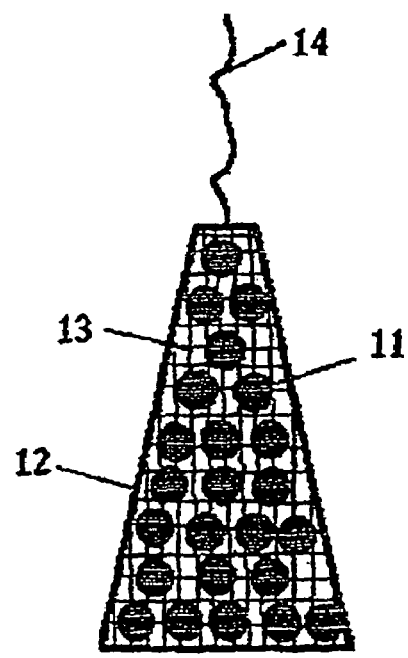
FIG. 2 shows a side view of another design of the device utilized to concentrate target organisms.

FIG. 2 shows a different design of the device. The beads 11 coated with antibodies are contained in the enclosure 12 made of a grid 13, shaped like a tea bag. A non-wicking string 14 is attached to the upper part of the enclosure 12 allowing movement of the enclosure 12 in the solution, while disallowing the solution containing bacteria to wick up the string. The grid's 13 pore size is smaller than the size of the beads to assure that the beads stay within the enclosure. However, the pore size is large enough to allow bacteria to freely pass into the enclosure.

The food sample to be tested for the presence of the target organism is mixed with the appropriate pre-enrichment broth. The pre-enrichment broth is incubated at an appropriate temperature. Upon the beginning of the incubation period, or alternatively after several hours of incubation, the enclosure 2 is immersed into the broth containing the sample thereby exposing the beads having immobilized thereon monoclonal or polyclonal antibodies to the selected bacteria of interest. This is accomplished by lowering the device 2 into the solution and agitating it for at least 30 minutes and up to several hours. This step allows cell capture by the beads, and the creation of bead-target microbial cell complexes. The next step involves the separation of the beads with the bound target cells from the suspension containing the food particles and other mixed flora. This is accomplished by pulling the whole device out of the solution, using the rod 5. The device is subsequently washed several times in sterile saline or buffer solution. The washing solution is changed after each wash to remove non-bound organisms. Addition of detergents such as Tween-20 (0.51–0.1% w/v) or protamine to the incubation broth mixture usually decreases the non-specific adsorption. Tween-20 can be also used in the washing procedure to remove non-specifically bound cells. After the wash step a number of methods can be utilized to detect the presence of the target organism. Depending upon the particular detection method to be used, as explained below, the beads may or may not be separated from the enclosure after the wash step.

Several detection procedures can be used in conjunction with the current invention to detect the presence of the microorganism of interest. For example, the device can be inserted into a new growth broth that includes a dye indicator and the changes in the dye characteristics can be utilized to determine presence or absence of the target organism. The microorganisms do not need to be detached from the beads since attachment to the beads has no effect on their growth. Therefore cells can continue to multiply in the appropriate medium. Alternatively the beads can be removed from the enclosure and inoculated onto the surface of appropriate selective or differential agar. Another approach is to utilize an immunoassay. Most immunoassays require $10^3$–$10^5$ cells ml$^{-1}$, therefore the beads should contain enough cells to perform a direct immunoassay. Similarly, this method can be combined with DNA hybridization and amplification techniques such as PCR.

As can be seen from the above disclosure, the method of the invention is particularly characterized by the use of immunological beads contained in an enclosure to select out target microorganisms from the sample. The beads must be capable of effectively capturing the target microorganisms from the test sample, while not capturing significant numbers of other organisms that might be present at much higher numbers. However, the antibody used need not be totally specific to the target organism since an additional selection step is available at the end of the assay. The antibodies must be oriented with their binding sites outward to allow contact between the binding portion of the antibody and the target organism. The size of the beads must be larger than the size of the microorganism, to remain contained in the enclosure, while allowing the target organism to enter the enclosure and attach to the beads. The contact time between the beads and the target organism must be long enough to allow strong interaction. Several hours of interaction was found to yield the best results, i.e. the creation of strong interactions to produce high capture efficiency. After the completion of the incubation step the beads are removed from the solution, by the removal of the enclosure in which they are contained. The enclosure and the beads are washed several times, and the beads are transferred into the detection system.

CONCLUSIONS, RAMIFICATIONS, AND SCOPE

Accordingly, it can be seen that the new method and device can be utilized with a large volume of media, to concentrate a target organism, without the need to utilize only a portion of the pre-enrichment broth or a small volume of enrichment broth as required for magnetic beads. The invention provides a method and device that is less labor intensive, more rapid and lends itself to automation. Many different designs, for containing the beads during the various steps of the assay, can be utilized.

Obviously, many modifications and variations of the present invention are possible in light of the above techniques. Although the description above contains many specificities, these should not be construed as limiting the scope of the invention but as merely providing illustrations of some of the presently preferred embodiments of this invention. The invention may be practiced otherwise than as specifically described.

What is claimed is:

1. A method of separating target microorganisms from a suspension, comprising:

immersing a plurality of beads coated with at least one antibody material into the suspension, said beads being contained within the interior space of an enclosure having a pore size smaller than the size of said beads and larger than the size of the microorganisms, suspending the enclosure in the suspension thereby allowing the capture of the target microorganisms by said beads; and washing said beads to remove organisms not bound to said beads, thereby separating target microorganisms from the suspension.

2. The method of claim 1 wherein at least one detergent is applied in said washing.

3. The method of claim 1 further comprising agitation of said enclosure holding said beads in the suspension.

4. The method of claim 1 wherein the time period of agitation is at least 30 minutes.

5. The method of claim 1 wherein the time period of agitation extends for several hours.

6. The method of claim 1 including the addition of at least one detergent to the suspension to decrease absorption of non-specifically bound cells.

7. The method of claim 1 including the subsequent step of immersing the enclosure and beads in new growth broth.

8. The method of claim 7 including the addition of an indicator material to the new growth broth.

9. The method of claim 1 including the subsequent step of separating the beads from the enclosure followed by at least one test to reveal the microorganisms of interest.

10. The method of claim 1 wherein said enclosure further comprises means attached to the enclosure for moving the enclosure in the suspension and for subsequent removal of the enclosure from the suspension.

11. The method of claim 10 wherein said means attached to the enclosure for moving the enclosure in the suspension and for subsequent removal of the enclosure from the suspension is attached to an upper part of the enclosure.

12. The method of claim 1 wherein said enclosure is made of a grid material.

13. The method of claim 3 wherein said enclosure holding said beads in the suspension is agitated with a rod or string attached to the enclosure.

14. The method of claim 1 wherein said enclosure is in the shape of a teabag.

15. The method of claim 1 wherein said enclosure is cylindrical.

* * * * *